United States Patent [19]

Fenyo et al.

[11] Patent Number: 4,926,861
[45] Date of Patent: May 22, 1990

[54] METHOD FOR IN VIVO TREATMENT OF TUMOROUS TISSUES ON BODY SURFACES

[75] Inventors: Martha Fenyo, Budapest, Hungary; Helmut Borberg, Gladbach; Janos G. Kadar, Cologne, both of Fed. Rep. of Germany

[73] Assignee: Harrier Inc., Salt Lake City, Utah

[21] Appl. No.: 106,544

[22] Filed: Oct. 8, 1987

[51] Int. Cl.⁵ .............................................. A61N 5/00
[52] U.S. Cl. .................................................. 128/395
[58] Field of Search ............................. 128/395–398; 250/504, 225; 350/394

[56] References Cited

U.S. PATENT DOCUMENTS

| | | | |
|---|---|---|---|
| 3,127,513 | 3/1964 | Rupprecht | 250/504 |
| 3,510,198 | 5/1970 | Pace | 350/394 |
| 3,648,706 | 3/1972 | Holzer | 128/395 |
| 3,778,619 | 12/1973 | Carnel | 128/395 |
| 4,298,005 | 11/1981 | Mutzhas | 128/396 |
| 4,686,786 | 8/1987 | Fenyo et al. | 128/396 |

OTHER PUBLICATIONS

Mester et al., "Effects of Direct Laser Radiation . . . ", Arch. Derm. Research, 263, 241–245, 1978.
Greguss, "A Model of Nonthermal Laser Effects . . . ", Laser 77 Opto-Electronics, Conf. Proc., Munich, 1977.

Primary Examiner—Edward M. Coven
Assistant Examiner—Mark S. Graham
Attorney, Agent, or Firm—Michael N. Meller

[57] ABSTRACT

A method for in vivo treatment of tumorous tissues on body surfaces that comprises the step of irradiating said tissues by polarized light of predetermined intensity, this polarized light predominantly includes wavelength components exceeding 300 nm and substantially excludes ultraviolet components.

A new use of a light source emitting polarized light includes the application of said light source for irradiating tumorous tissues on body surfaces.

6 Claims, 11 Drawing Sheets

METHOD FOR IN VIVO TREATMENT OF TUMOROUS TISSUES ON BODY SURFACES

FIELD AND BACKGROUND OF THE INVENTION

The present invention relates to a method for in vivo treatment of tumorous tissues on body surfaces.

The medical literature dealing with various treatments of cancer is very extensive and the citation of only a small portion thereof would certainly make the present specification prolix. In spite of worldwide research and numerous significant achievements there have remained much to be solved and any small pace of improvement is significant.

It has been long known in the art that the irradiation of tumorous tissues by specific rays such as X-rays or isotopes have a growth inhibiting effect. Such treatments were based on the selective destructive effects of these rays for tumorous and healthy cells. A different branch of cancer research deals with chemotherapy.

Recently much effort is concentrated on the investigation of the immunotherapy with tumor-infiltrating lymphocytes. Of the pertinent literature a few number of papers will be cited. The first one is the work of Steven A. Rosenberg, Paul Spiess and Rene Lafreniere: 'A New Approach to the Adoptive Immunotherapy of Cancer with Tumor-Infiltrating Lymphocytes' (Science, Vol. 233, 19 Sept. 1986, pp. 1318–1321). The second reference is Richard L. Kradin and James T. Kurnick: Adoptive Immunotherapy of Cancer with Activated Lymphocytes and Interleukin-2 published in "The Year in Immunopathology, Pathol. Immunpathol. Res. pp. 193–202 (1986)". Rosenberg et. al have reported that the adoptive transfer of tumor-infiltrating lymphocytes (TIL) expanded in interleukin-2 (IL-2) has proved to be substantially more effective to mice bearing micrometastases from various types of tumors than lymphokine-activated killer (LAK) cells are. The combination of TIL and cyclophosphamide was further potentiated by the simultaneous administration of IL-2. Kradin et. al have disclosed that a measure of therapeutic success has been achieved by the administration of interleukin-2 (IL-2) and IL-2 activated lymphocytes in mice with metastatic malignancies. The Apr. 9, 1987 issue of the New England Journal of Medicine includes reports by two different groups of investigators concerning their experience with adoptive immunotherapy for cancer.

Our purpose of our citing these references was to demonstrate that there exists a certain degree of correlation between the responses of tumor cell on various treatments in mice and in humans.

In a quite different field of art a method has been suggested for the stimulation of biological processes relating to cellular activity, particularly for promoting the healing of wounds, ulcers and epithelial injuries which was based on the recognition that polarization property of laser light was responsible for the well-demonstrated wound-healing effect of laser light, thus the expensive and bulky laser could be replaced by a light source emitting incoherent polarized light. This invention is disclosed in U.S. Pat. No. 4,686,986 issued to Fenyö et. al, Mrs. Fenyö being one of the inventors of the present invention as well.

The polarized lamp has gotten a fairly moderate acceptance and its medical use has been rather limited. A few number of patent applications were directed to particular designs of polarized lights sources for biostimulation. Of these PCT publication WO-A-8 403 049 and published European patent application 84850395.9 can be mentioned as relevant.

SUMMARY OF THE INVENTION

The object of the invention is to provide a new method for in vivo treatment of tumorous tissues on body surfaces which can enhance the available arsenal of means and methods of overcoming or moderating this disease.

The essence of the invention is the recognition of the fact that polarized light (be it incoherent or laser light) can positively influence the tumor-host relationship leading to suppression or rejection of tumors. The exact mechanism of this effect remains to be elucidated.

According to the invention a method has been provided for in vivo treatment of tumorous tissues on body surfaces that comprises the step of irradiating said tissues by polarized light of predetermined intensity, this polarized light predominantly includes wavelength components exceeding 300 nm and substantially excludes ultraviolet components.

It is preferable if the intensity of irradiation is between 20 and 150 mW/cm$^2$, however, the highest intensity of the irradiation is limited only by the sensitivity of tissues against heat load concomittant with the irradiation.

It has been found that the effects of an irradiation with polarized light last about for 24 hours. This finding can be largely inaccurate, nevertheless it is preferable if the treatment is carried out at least once a day for at least one period of at least 2 minutes duration. It is preferable, if the time of the daily treatment is between 5 and 30 minutes. These time data are, however largely dependent on the individual, on the intensity and spectral distribution of the light, on the depth of the tissues to be treated and on several other factors.

In a preferable embodiment the polarized light includes polarized infrared components. With such components the depth of penetration will be higher than in case of using visible components only. A further advantage of using infrared components lies in the increased efficiency of utilizing the available light output of generally available light sources.

In a preferable embodiment the cross-section of the irradiating light is at least as large as the surface area of the tissues to be treated. By using a sufficiently large cross-section the need for mosaic-like irradiation is eliminated, and the time of treatment is reduced. If substantially larger areas are irradiated than the overall surface of the tumor tissues, the results can even be better, since due to limited penetration of the light into under-surface tissues (including arteries and veins) the stimulation can be more effective.

In a preferable embodiment the irradiating light can have a spectral distribution that corresponds substantially to that of a metal halogen bulb from which components under about 400 nm have been substantially filtered out.

According to the invention a surprisingly new use of a light source emitting polarized light with wavelength components exceeding 300 nm has been suggested, in which said light is used for irradiating tumorous tissues on body surfaces. The term 'body surface' covers areas in body cavities to which light can be administered as well as under-surface tissues within the range of penetration of polarized rays.

This new use covers light sources disclosed in U.S. Pat. No. 4,686,986 as well as other conventional light sources like laser sources used up to now for wound healing or general biostimulation.

DESCRIPTION OF THE PREFERRED EMBODIMENTS

All experiments were performed with inbred BALB/c mice of our own breeding colony originally derived from the Sloan-Kettering Memorial Institute (New York, USA). The used tumor was the methylcholanthren induced fibrosarcoma (BALB/c Meth A) originally derived from Dr. Old's Laboratory (Sloan-Kettering Memorial Institute).

The tumor was maintained in its ascites form through serial passage in the peritoneal cavity of BALB/c mice. The cells were harvested, washed three times in Hank's solution, examined for vitality and inoculated subcoutaneously (s.c.) into the abdomen of syngenetic mice. From previous experiments it is well known that the injection of $3 \times 10^6$ vital cells represent 100% take of the tumor. Therefore always this amount of cells was administered. For the experiments only male mice were used of more than 25 g body weight and of equal age and breed.

Figure 1:
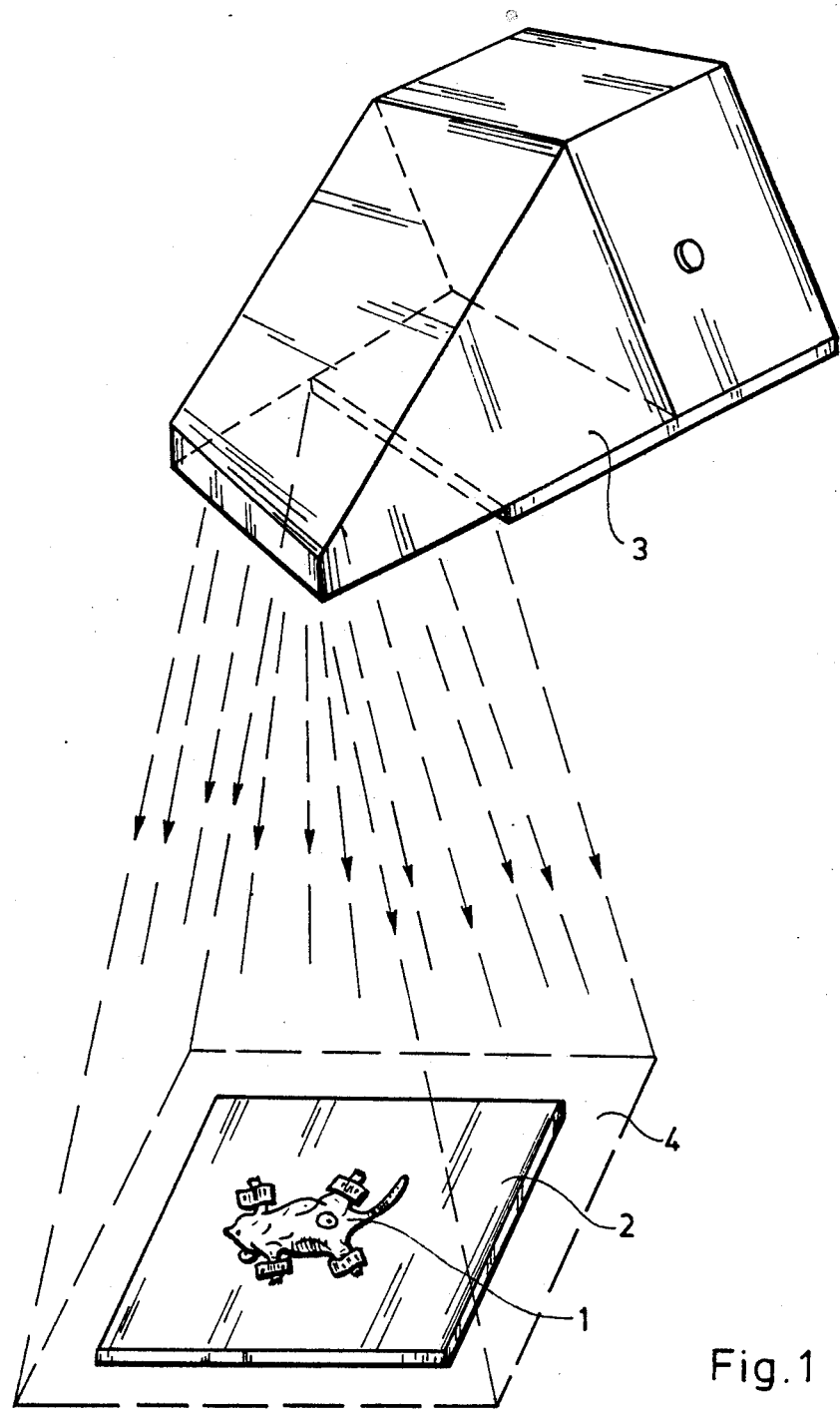
FIG. 1 shows how mice were irradiated with polarized light.

In the experiments 7 groups were formed, each included four or five mice. These groups were treated first after 48, 72 and 96 hours, respectively after transplantation and subsequently each day until their death by linearly polarized light. A group of four mice served as tumor bearing untreated control. The treatment consisted of irradiation by polarized light of about 50 mW/cm$^2$ power density using the lamp sold under the trade name EVOLITE by Bildsystem AB, of Malmö, Sweden, designed according to the published European patent application 84850395.9. FIG. 1 shows the general view of the irradiation arrangement. Mouse 1 under treatment was kept on its back and was temporarily fixed on a board 2. Light source 3 emitted parallel rays of polarized light having a rectangular cross-section of 200×300 mm indicated by reference numeral 4. The spectral distribution of the irradiating light was in correspondence with that of a usual metal halogen bulb, however, components under the wave length of about 400 nm were effectively suppressed. The distance of the treated surface of the mouse 1 from the exit opening of the light source 3 was about 18-20 cm. The cross-section of the irradiating light was larger than the whole surface of the mouse 1 therefore the irradiation was not limited to the tumorous area.

Each irradiation was performed under neurolept anaesthesia (Vetranquil 0.01% 0.1 ml intramuscular inj.). The duration of the daily irradiation was 5, 10, 15 and 30 minutes in the respective groups. Each day the mice were irradiated about the same time. Table 1 summarizes the data of irradiation for groups 1 to 6

TABLE 1

| Number | Group size | Time of the first treatment after tumor injection | Daily time of irradiation |
|---|---|---|---|
| 1 | 4 | 48 h | 30 min |
| 2 | 4 | 48 h | 15 min |
| 3 | 5 | 48 h | 10 min |
| 4 | 5 | 48 h | 5 min |
| 5 | 4 | 72 h | 30 min |
| 6 | 5 | 96 h | 30 min |

Figure 2:
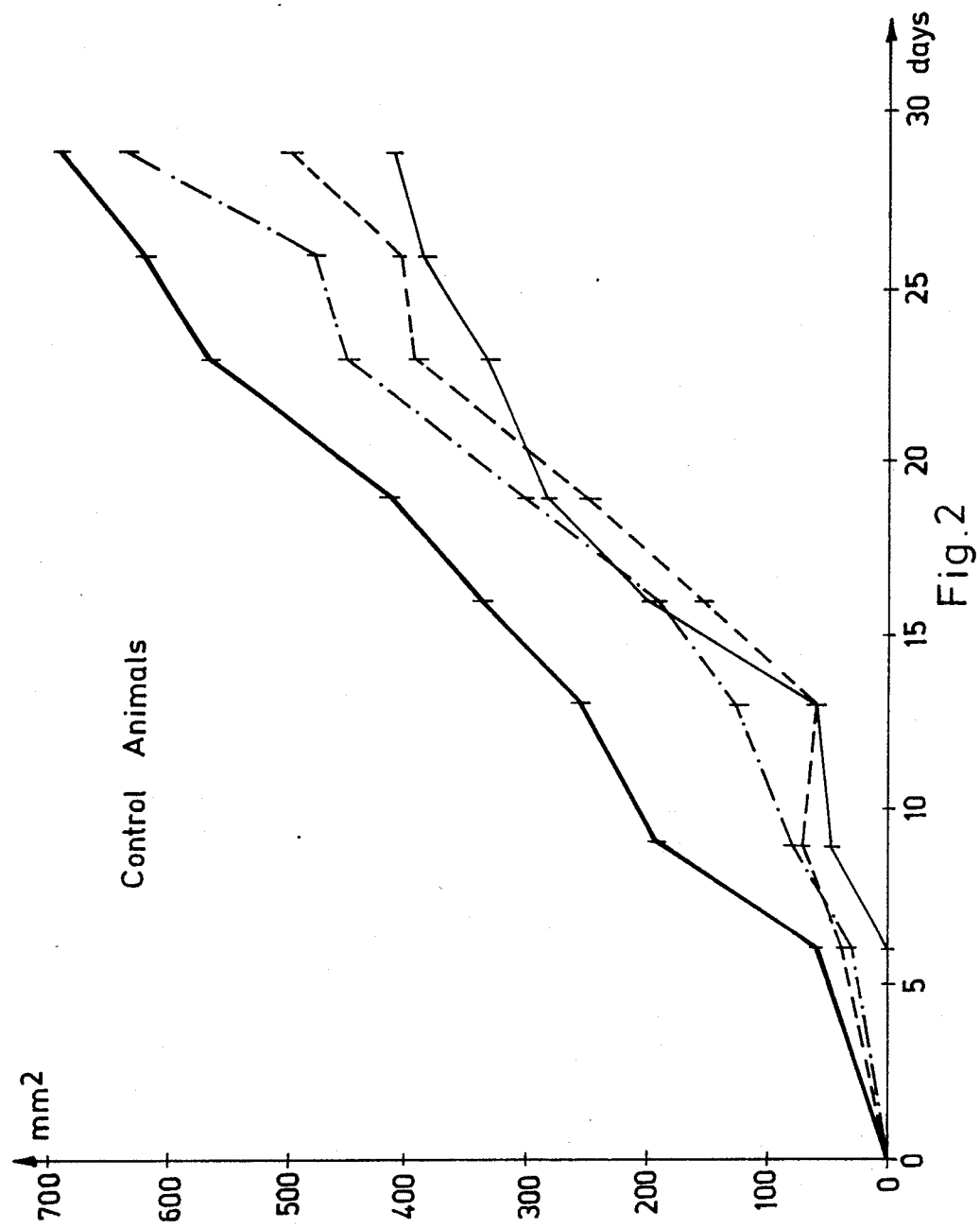
FIG. 2 shows the increase of tumor area versus time at the mice of the control group.
Figure 3:
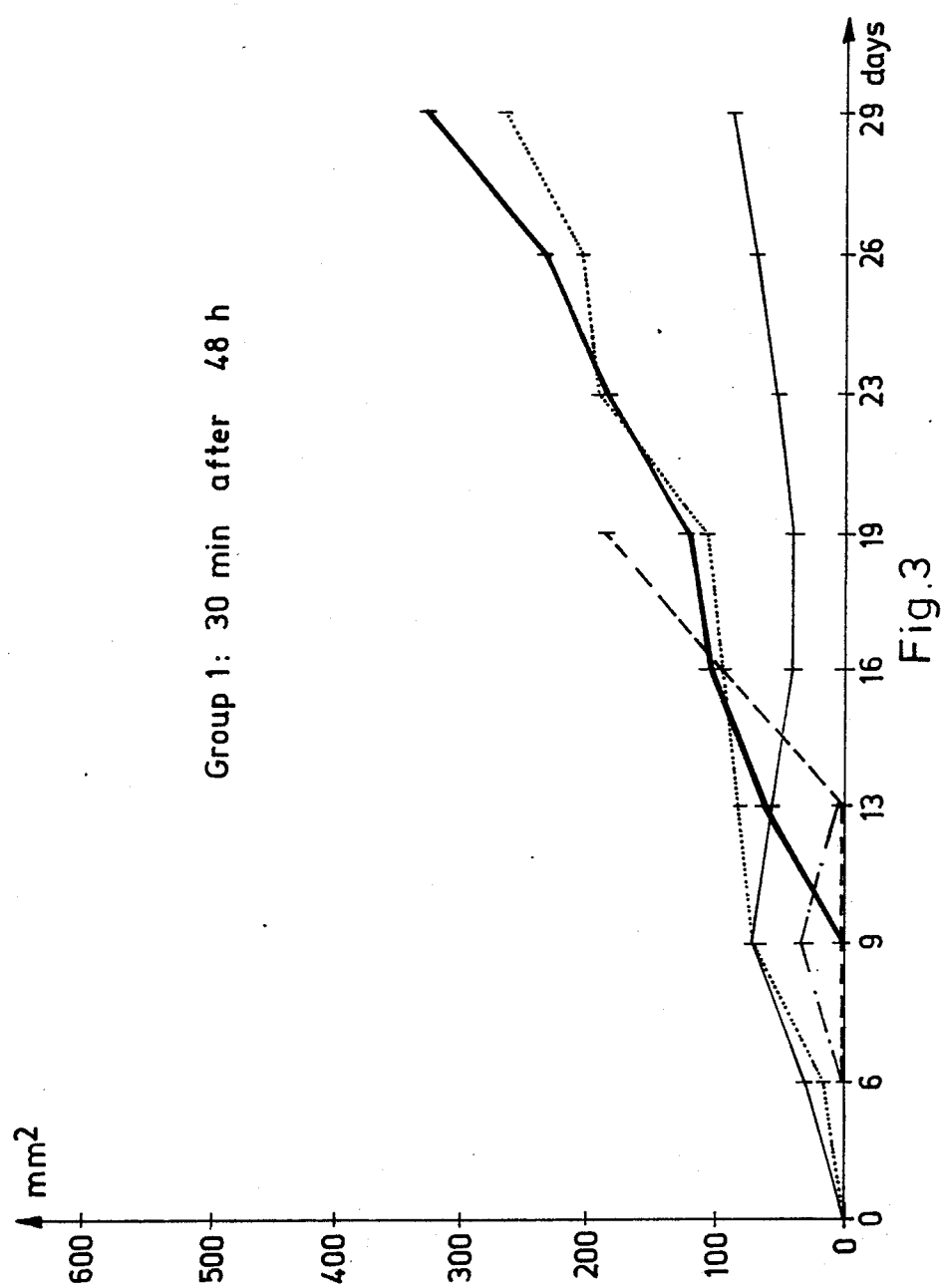
FIGS. 3 to 8 are curves similar to those of FIG. 2 relating to respective ones of six treated groups.
Figure 4:
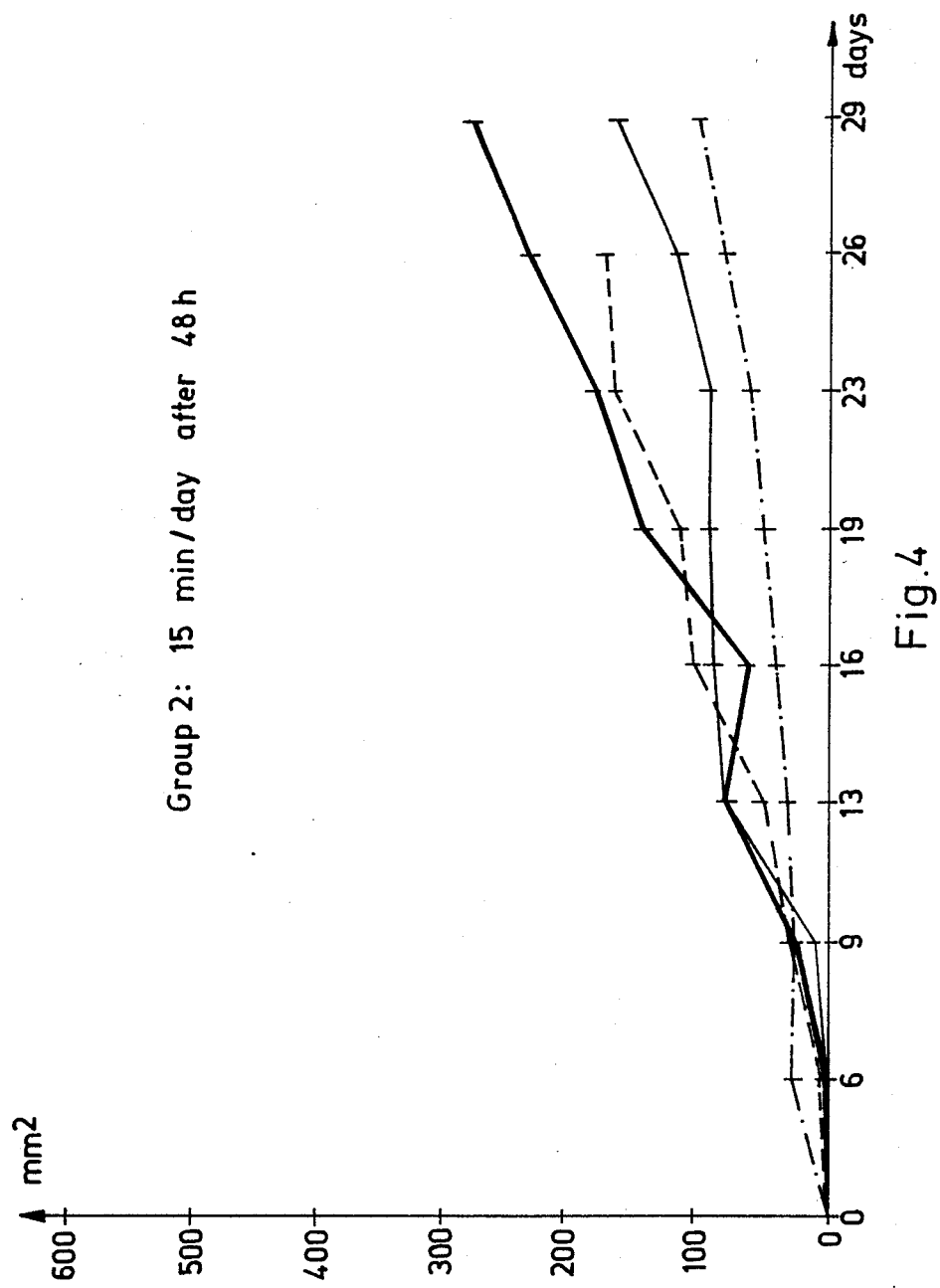
Figure 5:
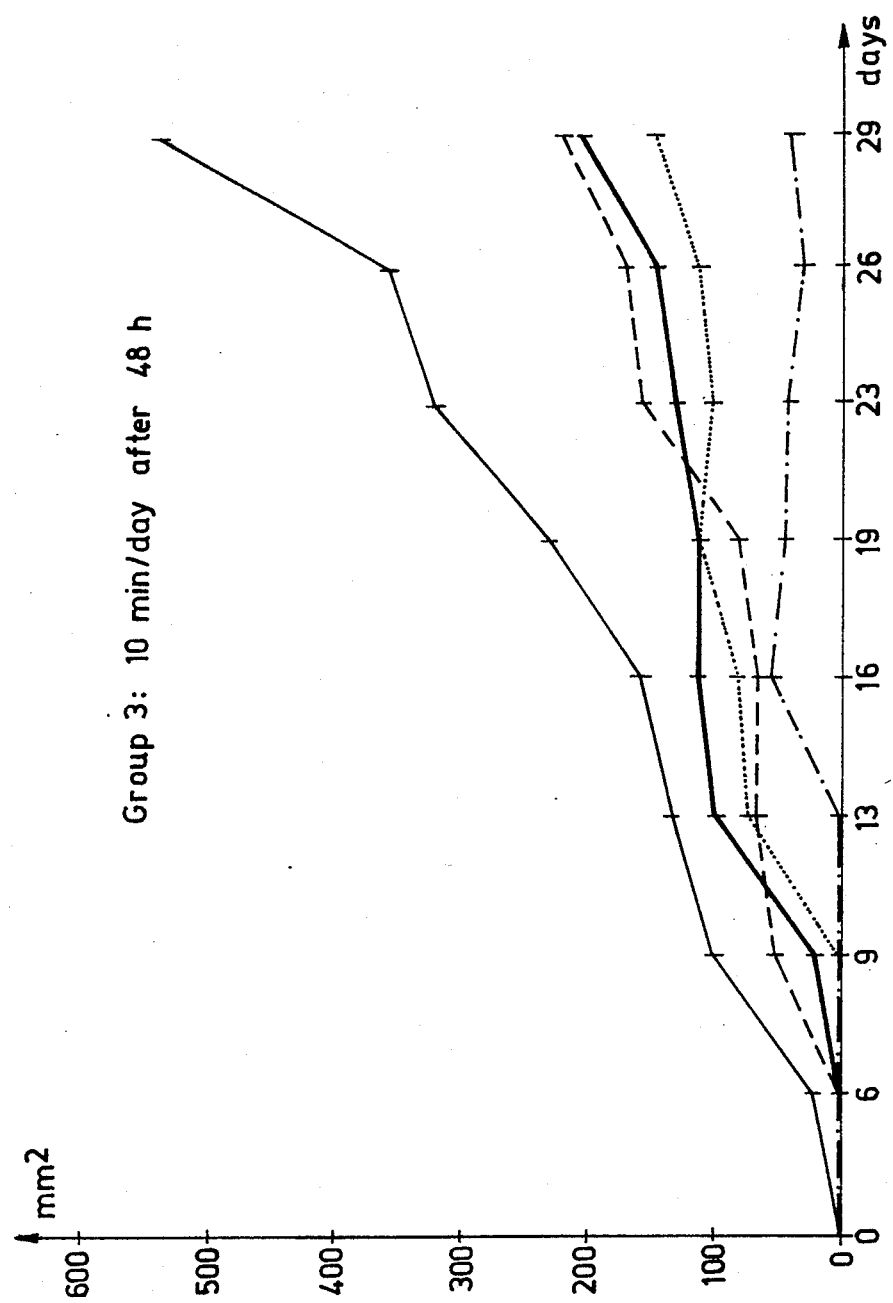
Figure 6:
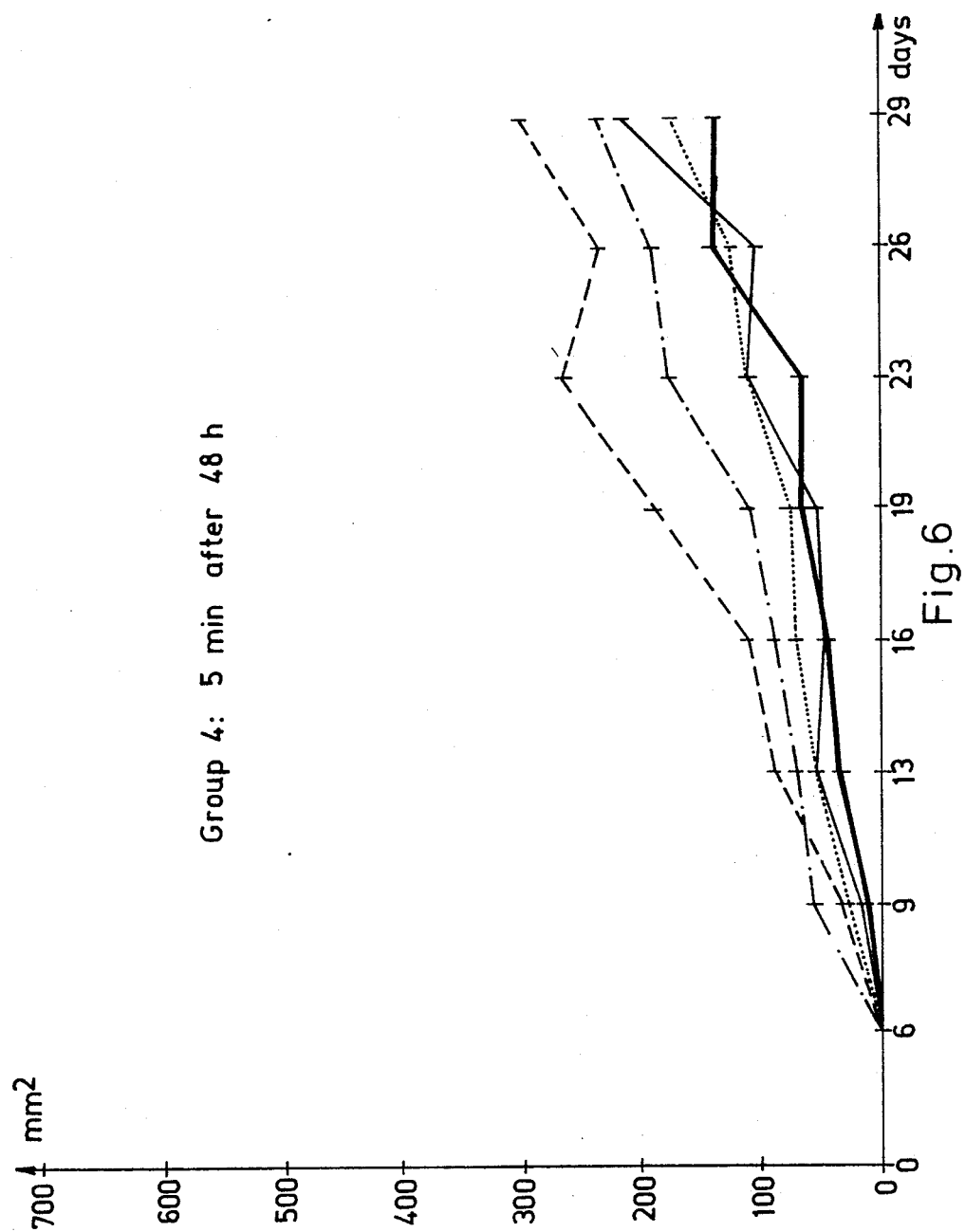
Figure 7:
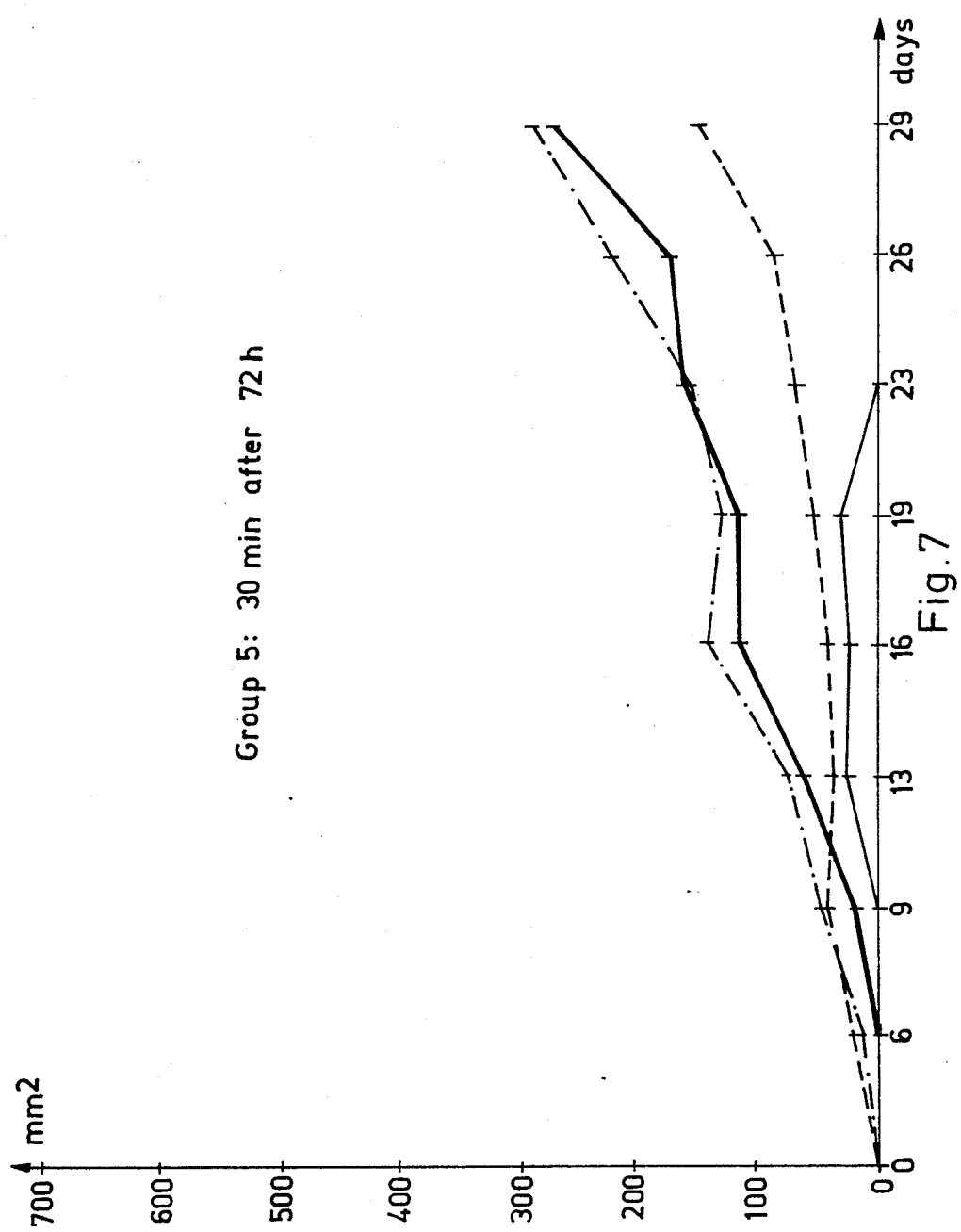
Figure 8:
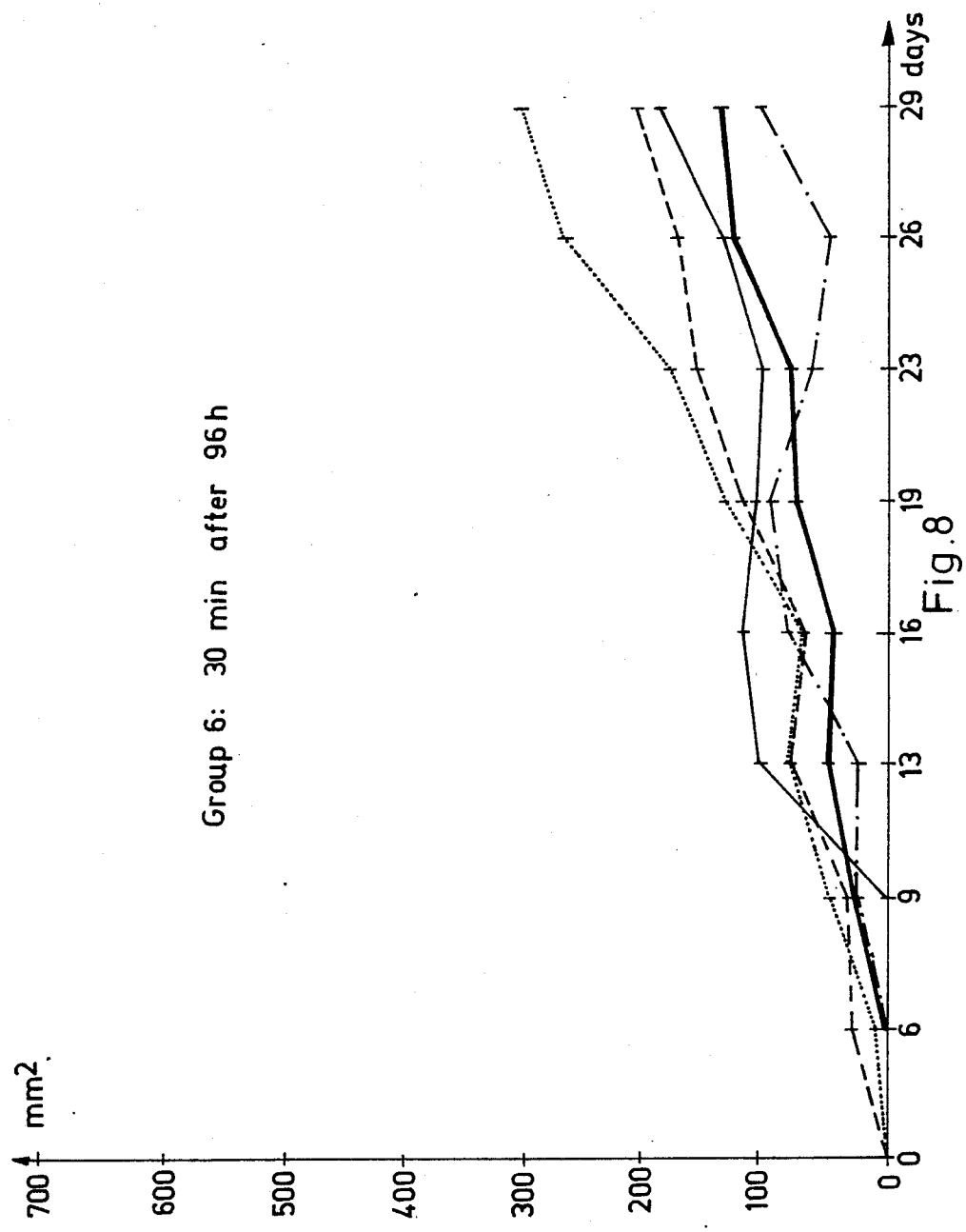

The growth of the tumor grafts was monitored twice every week by measuring the size thereof by means of calipers. The tumor size is expressed in mm$^2$ units obtained by the product of the largest two diameters of the tumor. FIGS. 3 to 8 illustrate the tumor growth as a function of time for the six groups. A similar diagram for the untreated control group is shown in FIG. 2.

Figure 9:
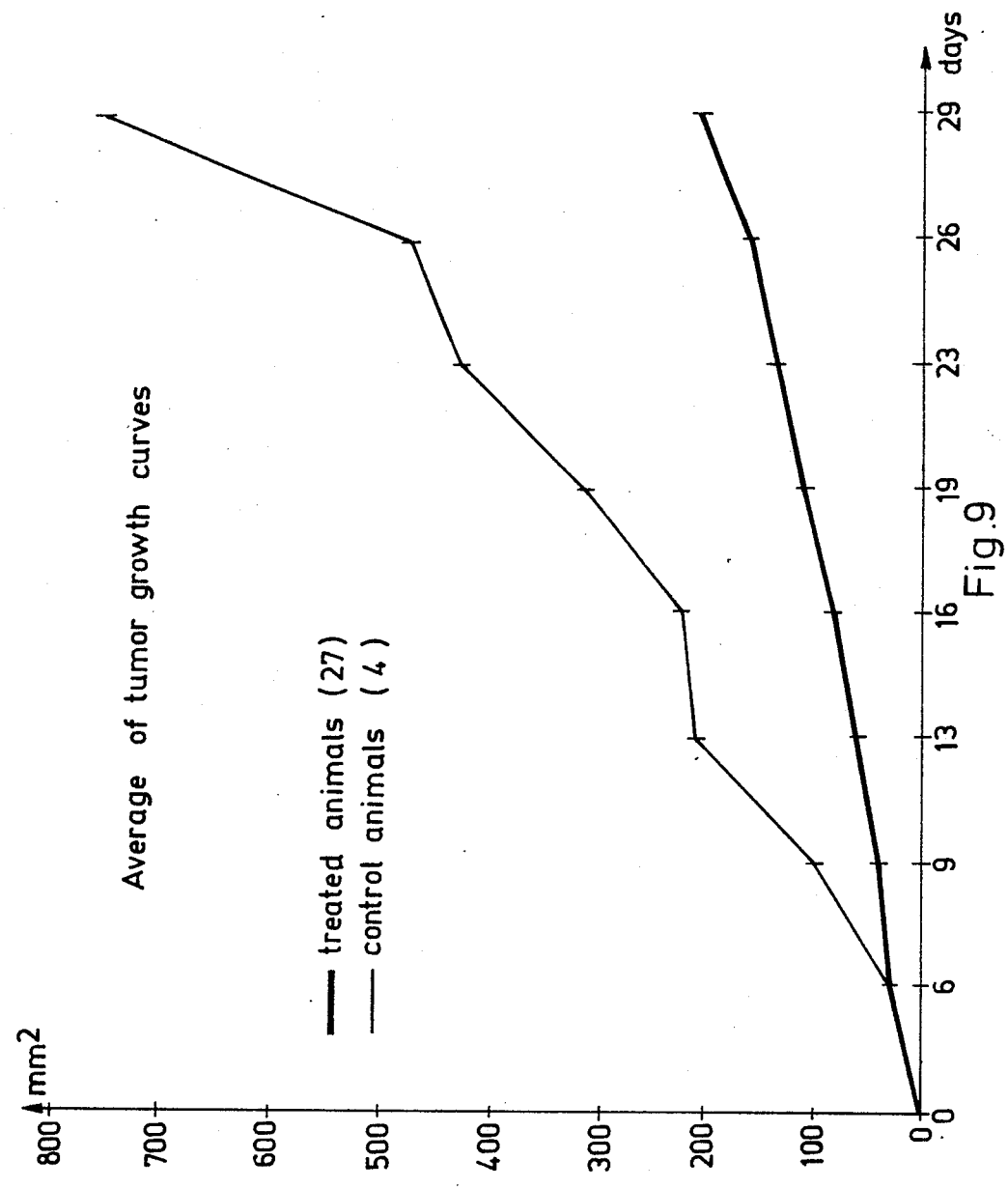
FIG. 9 shows the average of tumor growth curves.

On the basis of the measured data statistical work was performed by using Mann-Whitney test on the 23rd day and Wilcoxon test on the 29th day. The average of the tumor growth curves for the treated and for the control groups is shown in FIG. 9, while FIG. 10 illustrates the average tumor surface on the 29th day for the respective groups including the control group.

The tumor growth curves demonstrate without exception that the treatment with polarized light effectively inhibited tumor growth in each group. On the 23rd day the average surface area of the treated groups was only 31% of the average of the control group, while a similar ratio at the end of the 29th day was only 28%. FIG. 9 shows that the growth rate of the treated animals is practically constant from the 6th day to the end of the 29th day, while this rate in the control group was uneven, the steepness has increased with time.

Figure 10:
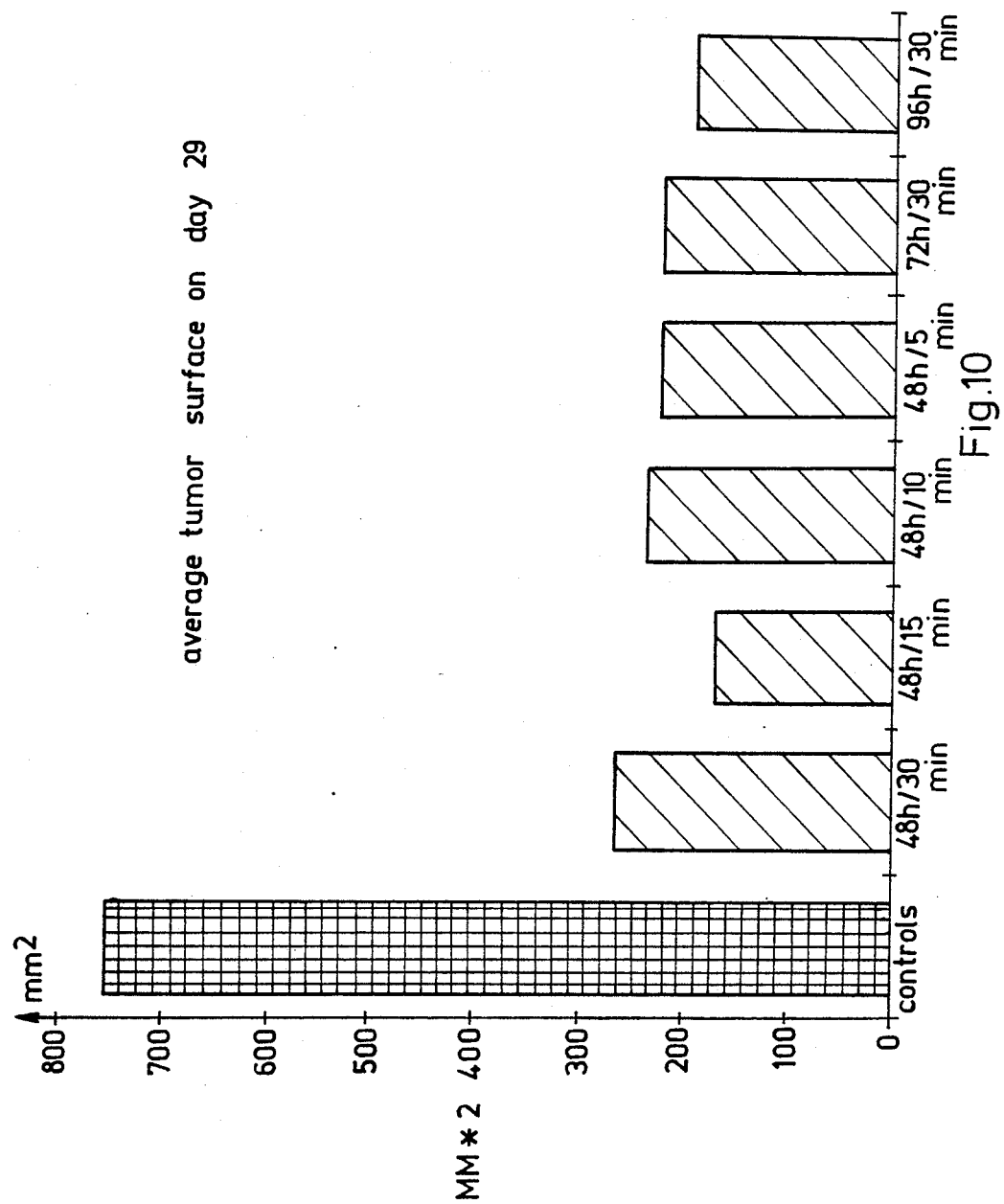
FIG. 10 shows the average tumor surface at the seven groups on the 29th day of treatment.

This fact is reflected also from FIG. 10, in which the group averages can be seen separately. This figure shows that there is no direct relationship between the irradiation time and the extent of response. The timing of the first treatment has probably more influence at least on the initial tumor growth. The survival of the animals was not investigated in this sort of experiments.

Figure 11:
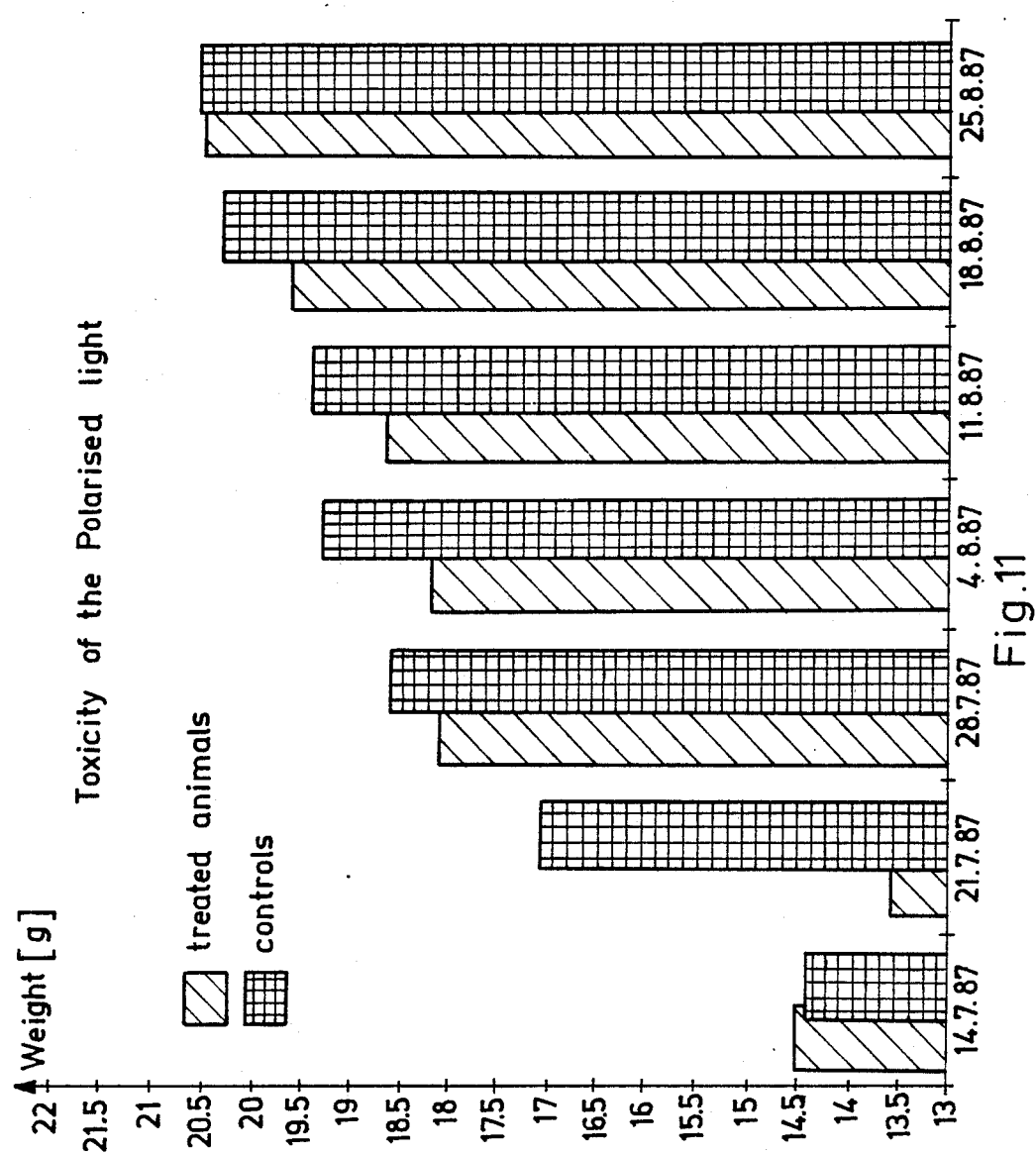
FIG. 11 shows the result of a toxicity test.

To exclude the possibility that a non-specific toxic effect of the polarized light can be responsible for the differences in the tumor growth, a separate toxicity test was carried out. In this test series 10 female mice were irradiated after weaning for twelve hours per day by polarized light. Another group of 10 similar mice was irradiated with non-polarized (normal) light with identical intensity, also for twelve hours a day. The increase of weight was measured for a longer period of time. The results of this test i.e. average weight of the respective groups versus time are illustrated in FIG. 11. This figure shows that apart from a slower weight increase in the first two weeks, the weight after the first month became very close to each other and by the end of the sixth week the average weight of both groups became equal. This demonstrates that the treatment with polarized light does not have a toxic effect on the experimentary mice, and the tumor growth inhibiting effects demonstrated by our tests are due to specific effects of polarized light on the tumor-host system.

Our experience with polarized light treatment on mice obtained during other series of tests than demonstrated here suggest that the effects of polarized light do not last longer than about 24 hours, and this explains why we have chosen the daily irradiation rate.

The essence of the test-series described hereinabove is the fact that polarized light with specific intensity can positively influence the tumor-host relationship leading to suppression or rejection of otherwise untreatable tumors. The exact mechanism of this effect remains to be elucidated.

There are, however, certain facts and phenomena which can assist in understanding the way how polarized light can accomplish its beneficial effects. It is known that the literature (Dvorak, H F; Senger, D R; Dvorak, A M: Fibrin as a component of the tumor stroma; origins and biologic significance, published in Cancer Metastasis Review 1983, 1 pp. 41–73) that the tumor structure is composed of malignant cells surrounded by stroma. The latter regulates the access of inflammatory cells to tumors. In many transplantable tumors lymphocytes are confined largely to the tumor-host interface and do not penetrate into mature tumor stroma or provisional matrix to any important extent (see also Dvorak, H F; Dvorak, A M: Immunhystochemical characterisation of inflammatory cells that infiltrate tumors; In: Haskil S. ed: Tumor immunity in prognosis: The role of mononuclear cell infiltration, Vol. 3 New York, Marcel Dekker 1982, pp. 297–307). According to recent investigations a well-defined permeability factor is produced by the tumor cells which renders local blood vessels permeable for protracted periods (See Senger, D R; Galli, S J; Dvorak, A M; Peruzzi, C A; Harvey, V S; Dvorak, H F: Tumor cells secrete a vascular permeability factor that promotes accumulation of ascites fluid, Science, 1983; 219: 983–5). The discrepancy between rapidly growing tumor cells and imperfect metabolic supply leads to necrosis which phenomenon is often referred to as spontaneous disappearing tumors (See Folkman J: Tumor angiogenesis, Adv. Cancer Res.: 1985; 43 pp. 175–203).

One of our interesting observations during the experiments was that central necrosis occurred earlier and to a greater extent than on the animals without polarized light therapy. Although such observations require more investigations, this can mature to a further verification that polarized light stimulates the immunological defense system.

The tumor used for the experiments belonged to a chemically induced type. It is known from our previous experiments (See Borberg, H; Abdallah, A; Schwulera, U; Sonneborn, H; Inhibition of tumor growth in a mouse fibrosarcoma after interleukin 2 application, Immunbiol. 172. 1986, pp. 383–390 and the references included therein) that the growth of chemically induced tumors can be inhibited by means of non-specific immunostimulants, by lymphocytes from immunised donors and soluble products of activated lymphocytes. The fact, that polarized light proved to be beneficial for decreasing the growth rate of a chemically induced tumor, can also be regarded as a further support for the hypothesis that the mechanism by means of which polarized light can be effective is the general stimulation of the immune system.

In view of the present invention and of the above outlined hypothesis the experiments obtained with wound healing obtain a new interpretation. In such tests the compositions of the wound secretions before and after treatment with polarized light were examined and compared to each other. The treatment resulted in a significant increase in immunoglobulins and other proteins. Also the cellular composition showed a marked difference: among neutrophil granulocytes lymphocytes and monocytes appeared and demonstrated activity within the wound secretion. These had to be caused by changes of the vascular permeability and/or subsequent chemotactic efforts which were otherwise lacking. The second reason why the particular references dealing with the adoptive immunotherapy of cancer were cited in the description of the prior art portion of the present specification will now be understood. In broad sense these papers have pointed out that an increase in activity of lymphocytes at the close proximity of tumor cells had beneficious effects. The above demonstrated increase in activity of the immune system in response to irradiation with polarized light can cause similar effects, thus it can be expected that the irradiation with polarized light can be an alternative (or complementary) to the administration of IL-2 and/or IL-2 activated lymphocytes.

It might be significant that during the experiments not only the tumor area, but the whole body of the mice was irradiated. Since polarized light with infrared components has certain depth of penetration in tissues, it can be expected that a treatment with polarized light on human applications can be more effective if irradiation is not limited physically to the tumor areas.

A major advantage of the method according to the invention lies in the harmless applicability thereof. Further to the above described toxity tests it can be added that polarized light treatment has been in use for more than six years for wound healing, cosmetical and other related applications in several countries and thousands of patients were treated therewith. Not a single case was reported with any side effect.

We claim:

1. Method for in vivo treatment of tumorous tissues on body surfaces comprising the step of irradiating said tissues by polarized light of predetermined intensity, said polarized light predominantly including wavelength components exceeding 300 nm and substantially excluding ultraviolet components, wherein said intensity is between 20 and 150 mW/cm$^2$, and wherein said step of irradiation is carried out at least once a day for at least one period of at least 2 minutes duration.

2. Method of claim 1, wherein said polarized light includes polarized infrared components.

3. Method of claim 1, wherein said light has a cross-section at least equal to the surface area of said tissues.

4. Method of claim 1, said light having a spectral distribution substantially corresponding to that of a metal halogen bulb from which components under about 400 nm have been substantially filtered out.

5. Method of claim 1, wherein said irradiation step is carried out once a day for a period between 5 and 30 minutes.

6. Method of claim 1, wherein said light comprises substantially parallel rays with substantially uniform spatial energy distribution.

* * * * *